(12) United States Patent
Fiechter

(10) Patent No.: US 11,460,378 B2
(45) Date of Patent: Oct. 4, 2022

(54) AUTONOMOUS SOIL SAMPLER

(71) Applicant: RogoAg LLC, Keystone, IN (US)

(72) Inventor: Troy Fiechter, Brookston, IN (US)

( * ) Notice: Subject to any disclaimer, the term of this patent is extended or adjusted under 35 U.S.C. 154(b) by 0 days.

(21) Appl. No.: 17/068,137

(22) Filed: Oct. 12, 2020

(65) Prior Publication Data

US 2021/0025790 A1     Jan. 28, 2021

Related U.S. Application Data

(63) Continuation-in-part of application No. 15/829,194, filed on Dec. 1, 2017, now Pat. No. 10,801,927.

(51) Int. Cl.
| | | |
|---|---|---|
| *E21B 49/00* | (2006.01) | |
| *A01B 33/12* | (2006.01) | |
| *G01N 1/08* | (2006.01) | |
| *G01N 1/28* | (2006.01) | |
| *G01N 35/00* | (2006.01) | |
| *G01N 33/24* | (2006.01) | |

(52) U.S. Cl.
CPC ............. *G01N 1/08* (2013.01); *G01N 33/24* (2013.01); *G01N 35/0099* (2013.01); *G01N 35/00732* (2013.01)

(58) Field of Classification Search
CPC ........... E21B 49/00; E02D 1/04; E02D 33/12; E02D 77/00; G01N 1/08; G01N 1/28; G01N 1/02; G01N 2001/282; G01N 2033/245
See application file for complete search history.

(56) References Cited

U.S. PATENT DOCUMENTS

| | | | | |
|---|---|---|---|---|
| 5,435,399 A | * | 7/1995 | Peterson | ................ E02D 1/04 |
| | | | | 175/135 |
| 6,016,713 A | * | 1/2000 | Hale | ................ A01B 79/005 |
| | | | | 73/864.45 |
| 6,138,522 A | * | 10/2000 | Miyoshi | ................ E21B 49/02 |
| | | | | 73/863.45 |
| 8,955,401 B1 | * | 2/2015 | Burton | ................ E21B 7/027 |
| | | | | 73/864.45 |
| 10,444,122 B2 | * | 10/2019 | Covely | ................ E02D 1/04 |
| 10,801,927 B2 | * | 10/2020 | Fiechter | ................ G01N 1/02 |
| 2003/0112152 A1 | * | 6/2003 | Pickett | ................ A01B 79/005 |
| | | | | 340/870.07 |
| 2011/0314938 A1 | * | 12/2011 | Anderson | ................ G01N 1/08 |
| | | | | 73/864.43 |
| 2018/0124992 A1 | * | 5/2018 | Koch | ................ A01D 41/127 |
| 2018/0156697 A1 | * | 6/2018 | Fiechter | ................ G01N 1/02 |
| 2018/0168094 A1 | * | 6/2018 | Koch | ................ A01C 7/203 |
| 2021/0025790 A1 | * | 1/2021 | Fiechter | ............. G01N 35/0099 |

* cited by examiner

*Primary Examiner* — Daniel P Stephenson
(74) *Attorney, Agent, or Firm* — Gutwein Law; Greg N. Geiser

(57) ABSTRACT

An autonomous soil sampling device. The device including a vehicle for generally autonomously navigating a given area for sampling and adapted with systems to generally avoid obstacles during maneuvering. The device including a soil sampling system designed for placement on a platform of the vehicle and including an extraction arm having a probe and auger to probe into the soil for extracting a quantity of soil. The extraction arm received on a housing and including a pair of rails to enable movement of the probe and auger and a collection bucket for depositing the quantity of extracted soil into a packaging assembly for collection, labeling, and storage of the individual samples.

3 Claims, 10 Drawing Sheets

AUTONOMOUS SOIL SAMPLER

CROSS REFERENCE TO RELATED APPLICATIONS

This application is a continuation-in-part of application Ser. No. 15/829,194 filed 1 Dec. 2017 and issued as U.S. Pat. No. 10,801,927 which claims priority to U.S. Provisional Patent Application No. 62/428,856 filed 1 Dec. 2016 to the above named inventor, and is herein incorporated by reference in its entirety.

FEDERALLY SPONSORED RESEARCH OR DEVELOPMENT

Not Applicable

SEQUENCE LISTING, A TABLE, OR A COMPUTER PROGRAM

Not Applicable

FIELD OF THE INVENTION

This invention relates generally to soil sampling techniques and equipment to facilitate accurate soil sampling in the agricultural setting.

BACKGROUND OF THE INVENTION

In the agriculture industry, it is known that accurate, reliable soil sampling has always been challenging. Soil testing is common and necessary in the agricultural industry to determine the soil type and nutrient levels such that crop production can be maximized. Typically, soil testing requires that soil samples or specimens be taken in the field, and then shipped off-site for laboratory analysis. A person normally operates the soil sampling machine or vehicle and records the location where the samples are taken. The workers are usually inexperienced and tend to compromise the accuracy of the samples. Human error is prevalent. For example, the samples may be inconsistent in size, improperly packaged, taken from the incorrect location, or comingled with other samples.

Soil sampling needs to be done in the exact same location year to year to see how field nutrient values are changing. Typical soil sampling methods use GPS technology but not automatically guided vehicles, therefore, the actual location year to year can very even hundreds of feet.

There exists a need to efficiently secure reliable, soil samples. Moreover, current soil sampling procedures take a long time to process at an off-site soil lab. Further, it is expensive and requires the use of toxic materials that are discarded as toxic waste. There is a desire to have the soil or tissue information as soon as possible, and there exists a need to have certain data related to soil samples processed in conjunction with the soil sampling activity. Therefore, the primary objective of the present invention is the provision of an automatic system for accurately collecting soil samples in the field. Similarly, a further objective is to conduct in field analysis of the soil samples and transmit the data about the soil analysis to a remote site. Still further, it is an objective to provide an automated soil sampling device that prevents cross contamination, provides a consistent extracted soil sample, and provides an automated packaging assembly.

SUMMARY OF THE INVENTION

This disclosure is directed to an autonomous, un-manned machine that is capable of performing the typical tasks of soil sampling, such as driving to the location, soil extraction, soil packaging, and labeling. In another exemplary embodiment, the soil sampler can carry out soil diagnostics of nutrients and physical characteristics. Alternately, the device of the present disclosure can be integrated within a manned vehicle, wherein the sampling and driving continues autonomously but the sampled soil is placed into a container by an operator.

The autonomous soil sampler uses an auger to recover the desired amount of soil at the desired depth. The autonomous soil sampler has an auger on a probe that is mounted to a soil extraction arm to probe at least 12 inches into the soil (a depth known to facilitate nitrate sampling). In another exemplary embodiment, the soil extraction arm can probe at least 24 inches into the soil. The soil extraction arm is movable about the device to enable the transfer of sampled soil to a top of a packaging machine assembly to be packaged and labeled. The samples of different depth for nitrate (for example) samples are packaged and labeled differently from other soil samples. The soil extraction arm includes an auger cleaning mechanism in the form of a cleaning collar to generally scrape off the material that may be brought up by the auger after probing the soil. This helps ensure a quality sample is obtained within a sampling bucket and also cleans off the auger prior to obtaining the next soil sample.

The packaging machine assembly uses a sealed form and fill concept. Notably, it uses a forming collar with a printing surface on a forming tube. The sealed and printed bags are then conveyed to a holding bin of the packaging machine assembly. The packaging machine assembly can additionally utilize an integrated barcode reader to read pre-printed plastic in place of a printer. During packaging and assembly all of the samples bags are generally maintained in a connection, wherein the assembly generally seals the individual soil samples within a compartment of a larger sample sleeve unwound from a reel. This sample collection configuration helps to main sample organization.

The soil extraction arm may be mounted to the back of a platform or positioned about a side of a vehicle and is generally movable about a track to facilitate soil sampling. The soil sampling is taken as the soil extraction arm moves from a stored position to a sampling position adjacent to the soil surface. The bucket containing the soil sample can also swivel or pivot about the extraction arm to allow for dumping into the packager or alternately, the bucket is positioned in a fixed assembly and soil is extracted from the bucket through a vacuum system. The pivoting bucket is able to dump the soil sample in the packager for further processing. In yet another alternate embodiment, the bucket may be removed from the extraction arm by the operator to facilitate manual dumping of the sampled soil into a container.

In another exemplary embodiment, the device includes a pair of sampling buckets. The pair of sampling buckets adapted to independently collect a sample from different depths.

In another exemplary embodiment, the soil sample from the bucket can be directed into a soil analyzer. The analyzer can analyze and determine the characteristics of the soil sample in real time. A computer system communicatively coupled to the analyzer can record and transmit the data recorded and relate the data to a specific location of the tested property. Additionally, the system can provide real-time updates as the soil samples are taken and packaged allowing a user to monitor the progress of the sampler. In one exemplary embodiment the sampler arm can enter into the exact same hole to bag or analyze different and separate profiles of the soil (e.g. bag up 0-6" differently than 0-12" or 12-24"). This allows for a layered analysis of the soil at the sample point.

In another exemplary embodiment, the sampler can still bag the samples from the bucket and establish a queue to be analyzed by the analyzer as the sampler collects additional samples. Samples that are analyzed can then be discarded back into the field or re-bagged for further testing. This can allow for greater efficiency in the collection and analysis process.

In one embodiment, the platform can be a part of any all-terrain vehicle commonly utilized as a multipurpose, rugged utility vehicle, such as a Kubota RTV, a John Deere Gator, a Polaris Ranger, Kawasaki Mule, Bobcat 3400 or a similar vehicle, such as a small tractor, that comprises a bed that may be used to support the packaging machine assembly and the soil extraction arm. The soil sampler of this invention may also be a purpose-built vehicle that does not include seating for passengers. The vehicle can include a generator rack to house a generator. The generator rack can be moveable to allow easy access to the generator. The generator can help power the soil extraction arm and packaging machine assembly of the device.

The autonomous soil sampler will detect if the bit or probe has become clogged, dirty, or is positioned on an object other than soil (such as a corn stalk) by using any known detection technique, such as an array of lasers or load cell. The autonomous soil sampler will also detect if the soil container did not get filled for some reason. Detecting insufficient soil filling will cause the machine to shut down and call for a human operator to inspect the problem. The autonomous soil sampler will also be able to detect rocks or other obstruction preventing adequate soil sampling, and in turn, probe in an alternate and different location.

The autonomous soil sampler will be able to navigate through the route and probe locations autonomously in a safe, predictable fashion. To that end, the autonomous soil sampler comprises obstacle detection and obstacle avoidance software and hardware features. It has the capabilities to detect potholes, ditches, humans, animals, rough patches, mud holes, severe grade, etc. If the autonomous soil sampler cannot plan a path around a certain obstacle, it will simply wait for the obstacle to move or for a human operator to resolve the issue. The soil sampler will also have a specified operating boundary that it cannot leave. The obstacle avoidance and navigation systems are generally provided with various components to aid in this detection and avoidance, including, but not limited to two dimension (2D) or three dimensional (3D) LIDAR (Light Detection and Ranging) for locating objects that may be in the path of the vehicle during operation.

The autonomous soil sampler will also communicate with the auger if a mud hole has been detected. It will then try probing in a different, but proximate, location to the originally desired testing location. The sampler can also record such incidents when the sampler must take a sample in an alternate but proximate location. This will allow a user to track when the soil samples are not recorded in the desired position or if the sample was not properly obtained to ensure that future samples are not affected or to correlate to previous samples taken.

Before entering each field, the operator can retrieve an image of the field and overlay either a zone management map, soil map, yield map, or similar data input. This will then allow the operator to identify where the samples should be taken. The operator will then mark the outside boundary of the field to designate the perimeter beyond which the autonomous soil sampler cannot travel. The operator will also mark out any known obstacles that could cause harm, damage, or restriction to the autonomous soil sampler or others. Any other obstacles will be detected by the soil sampling machine while traveling on the route through the various detection systems. Maps or routes can also be loaded into the sampler remotely through cellular or wireless data communications. Alternately, the operator may choose to operate the vehicle without the autonomous navigation features and drive the vehicle to the desired sampling locations.

All soil sampling components can be removed from the platform in an efficient manner, typically with customary equipment for handling heavy equipment, such as a forklift, or by using manpower. The platform can then be used for other regular farm tasks. The platform may be modified for the specific purpose of soil sampling. Moreover, the platform may be modified or a purpose-built machine may be created to follow crop rows to perform in-season soil or nitrate sampling.

The autonomous soil sampler can be used for various other applications such as: a) autonomous cover crop seeding, b) nutrient analysis of the soil (e.g. pH, H, P, K, OM, Mg, CA, etc.), c) physical soil characteristics of soil (e.g. filtration, compaction layers, CEC, etc., d) autonomous in-season tissue sampling, e) "follow-m options" to follow any other piece of equipment such as tiling, spraying, rock pick-up, f) autonomous field rock removal, g) un-manned and autonomous chemical spraying, h) autonomous field topography, i) one-row corn planting for planting the male row in seed corn production, and j) population counter for plants that are just emerging out of the ground. In some embodiments, the soil sample can be tasked with doing multiple application in a single pass of the field to optimize efficiency. In other embodiments, the soil sampler can take real-time measurements of other factors while obtaining the soil samples.

In another embodiment of the present disclosure, the use of LIBS (Laser-Induced Breakdown Spectroscopy) or other forms of LA-ICP-MS (Laser Ablation Inductively Coupled Plasma Mass Spectrometry) may be implemented on or off the platform to expand the capabilities beyond the autonomous soil sampler. The soil can be extracted the same way and then pelletized or mixed with a paraffin or other solution. The pellets can then be placed into an analytical system, such as a laser system, to be analyzed. A soil container also has the capabilities to perform pH testing.

For tissue sampling, the platform can navigate down crop rows and perform tissue sampling and nitrate testing at the same time. A tissue sampling arm can detect where the crop is located and retrieve a sample of leaf tissue. The tissue will then be dropped into the LIBS machine to acquire a quantification of the elements.

The LIBS machine can also be placed in the back of a truck to manually test the soil or tissue, while the platform travels and retrieves needed samples. These platforms for tissue sampling can be made small enough to perform plant analysis all through the growing season. The machine can also use ISFET (ion-sensitive field-effect transistor) or ISE (ion-selective electrode) sensors to measure certain elements such as Nitrate, Ammonium, P, K, etc.

Additionally, electrical conductivity, Raman Scattering, Lab on Valve (LOV), FIA (Flow injection Analysis), X-ray, Vibrational Spectroscopy, or other forms or spectrometry in addition to LIBS, ISE or ISFET sensors can be provided on the autonomous soil sampler. The soil conditioning equipment can be mounted as well to prepare the sample for a certain nutrient measurement. These preparations can include drying, grinding, insertion Hydrogen peroxide, blending, homogenizing, inserting nutrient extractants, pelletizing, etc.

BRIEF DESCRIPTION OF THE SEVERAL VIEWS OF THE DRAWING(S)

The accompanying drawings are included to provide a further understanding of the present invention and are incorporated in and constitute a part of this specification. The drawings illustrate exemplary embodiments of the present invention and together with the description serve to further explain the principles of the invention. Other aspects of the invention and the advantages of the invention will be better appreciated as they become better understood by reference to the Detailed Description when considered in conjunction with accompanying drawings, and wherein.

DETAILED DESCRIPTION OF THE INVENTION

Figure 1:
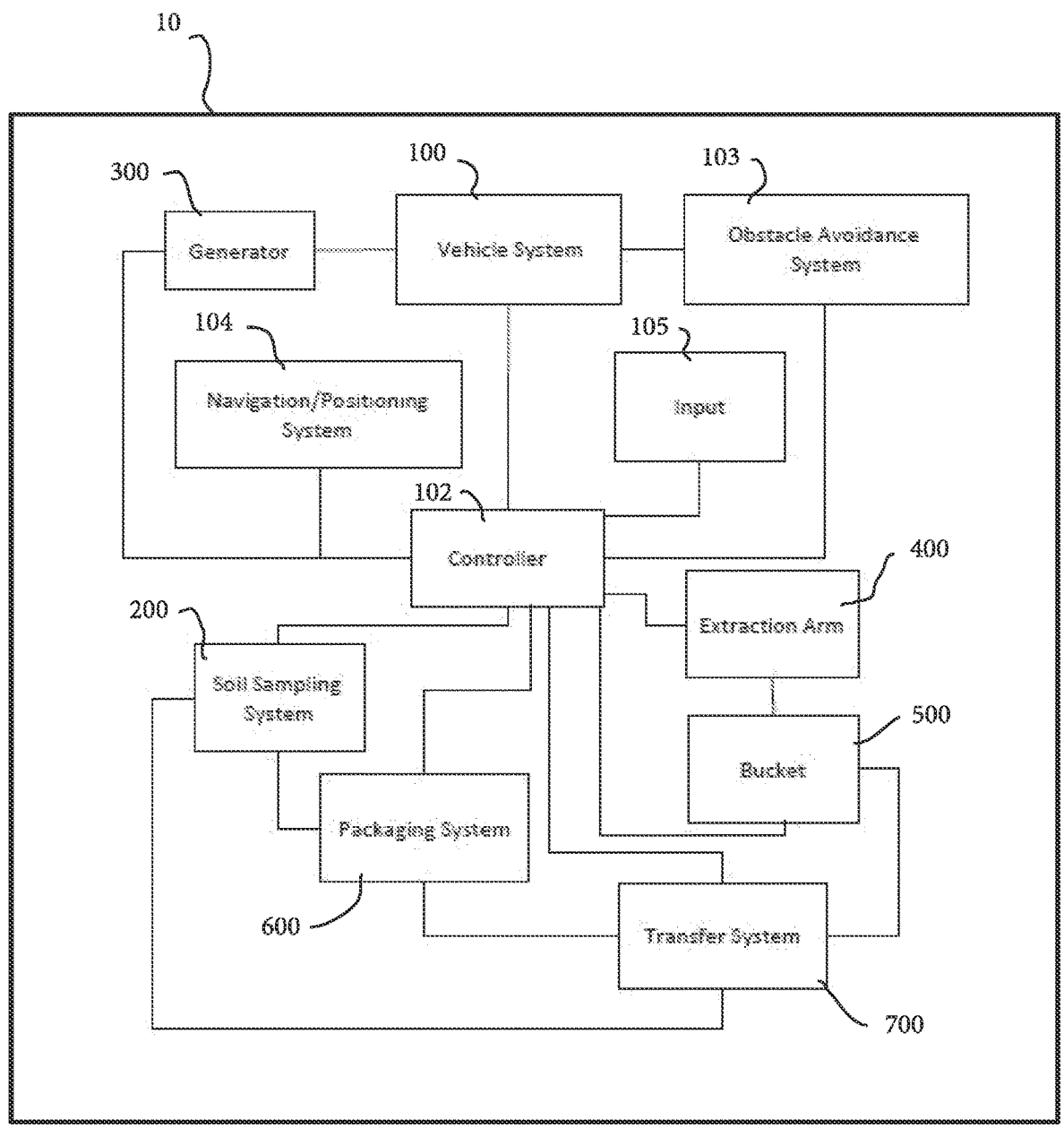
FIG. 1 shows a wire frame of the systems of the autonomous soil sampling device, according to the present disclosure.
Figure 2:
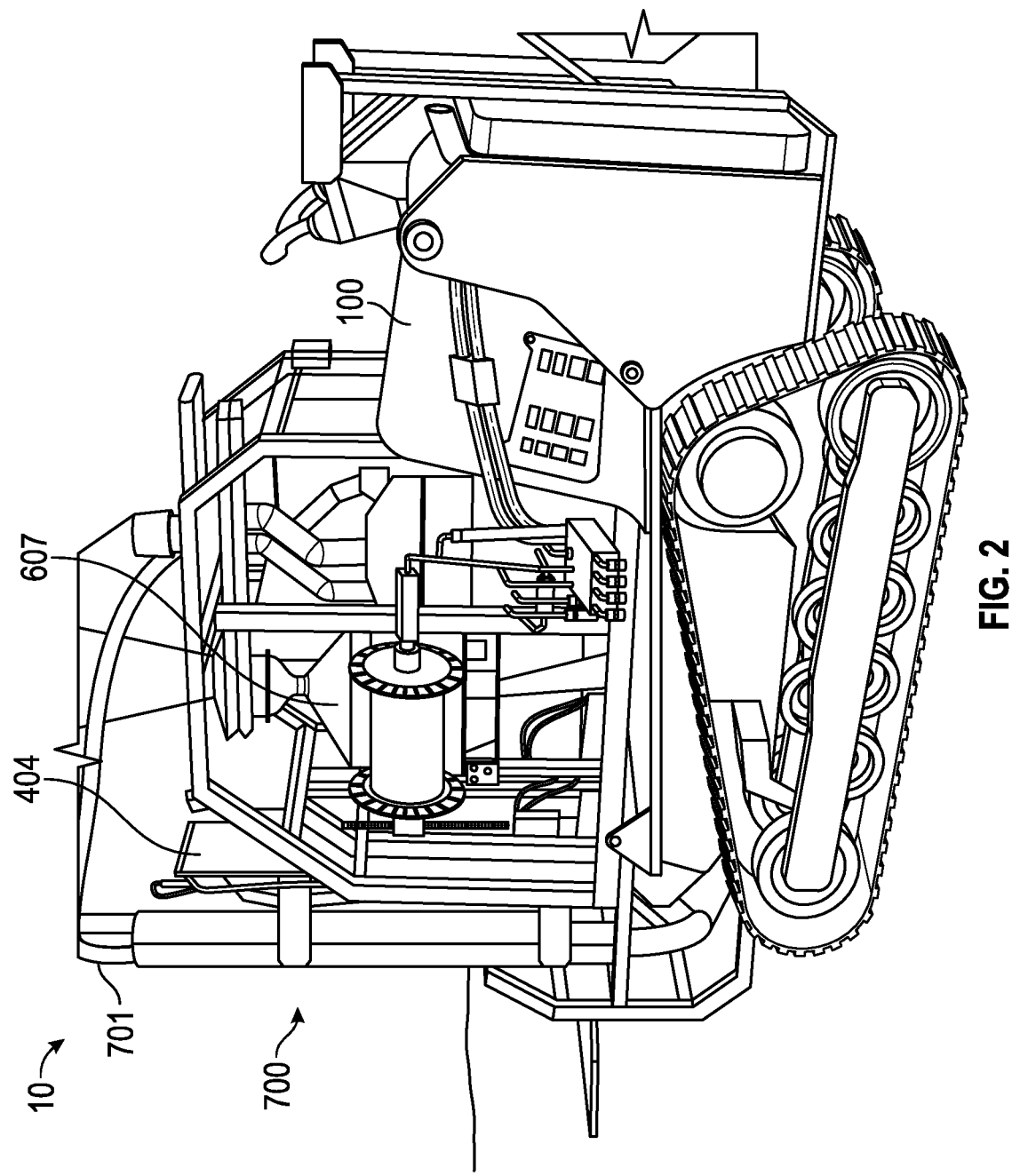
FIG. 2 shows an isometric side view of the sampling system and vehicle, according to the present disclosure.
Figure 3:
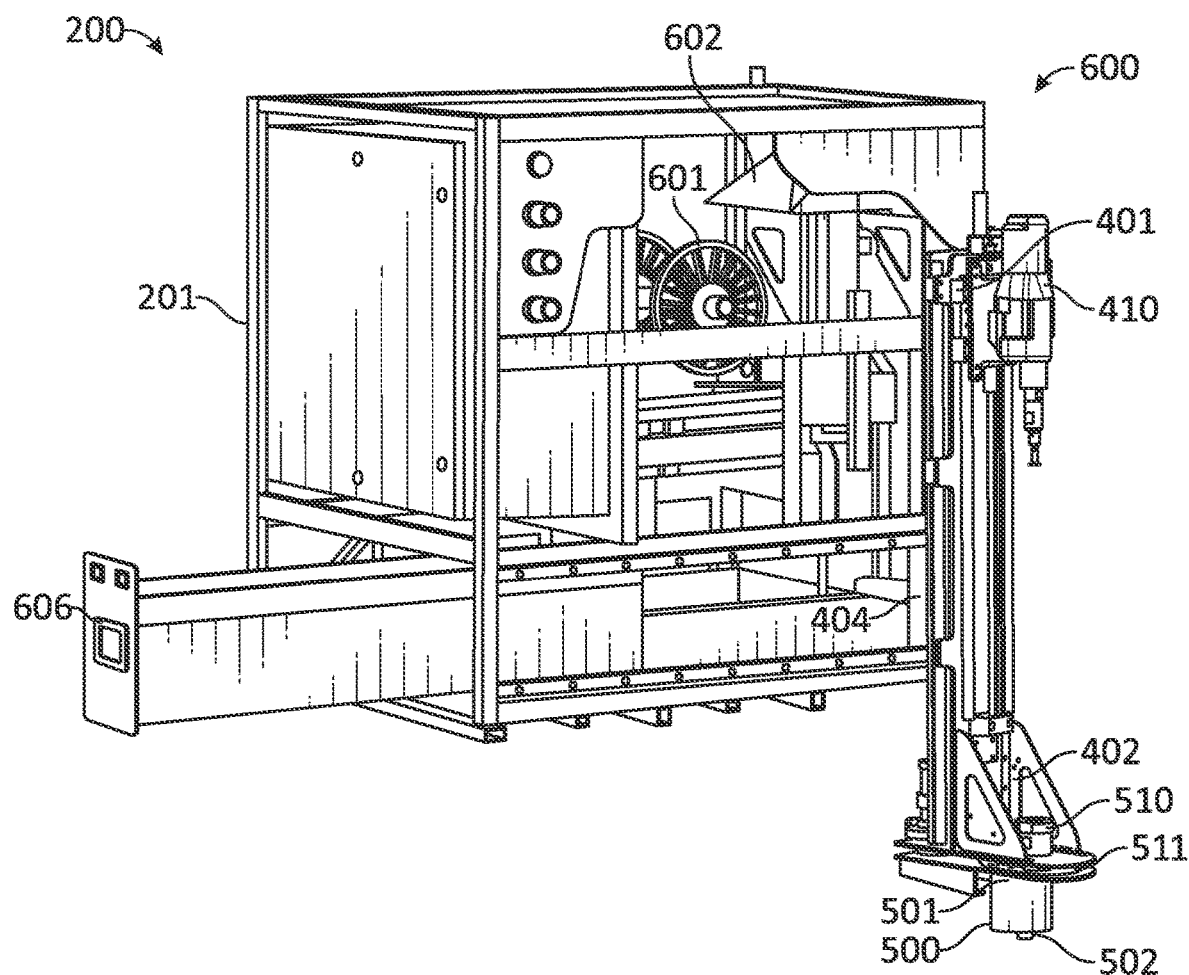
FIG. 3 shows an isometric rear side view of the sampling system with holding bin, according to the present disclosure.
Figure 4:
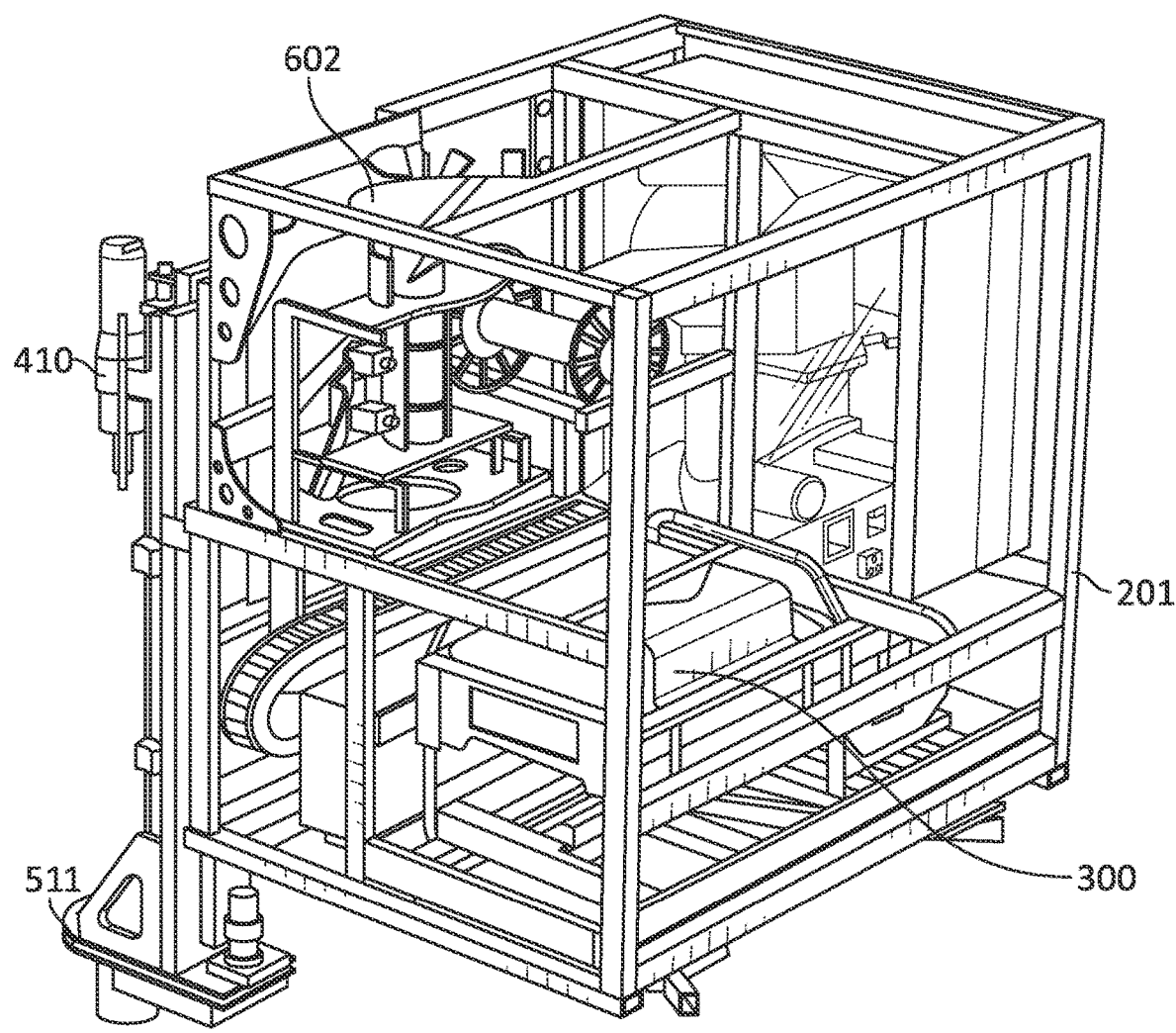
FIG. 4 shows an isometric view of the sampling system, according to the present disclosure.
Figure 5:
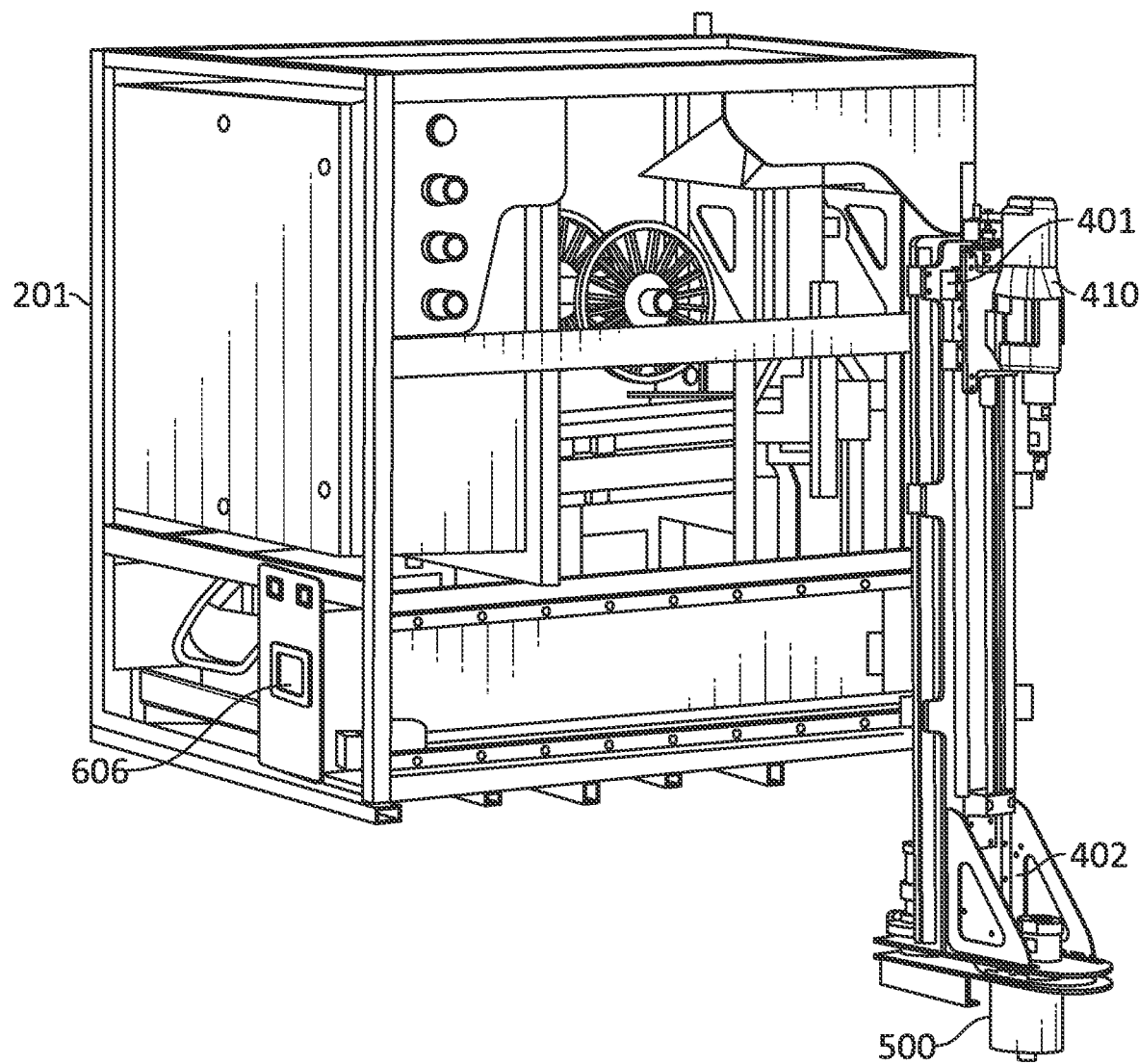
FIG. 5 shows an isometric view of the sampling system, according to the present disclosure.
Figure 6:
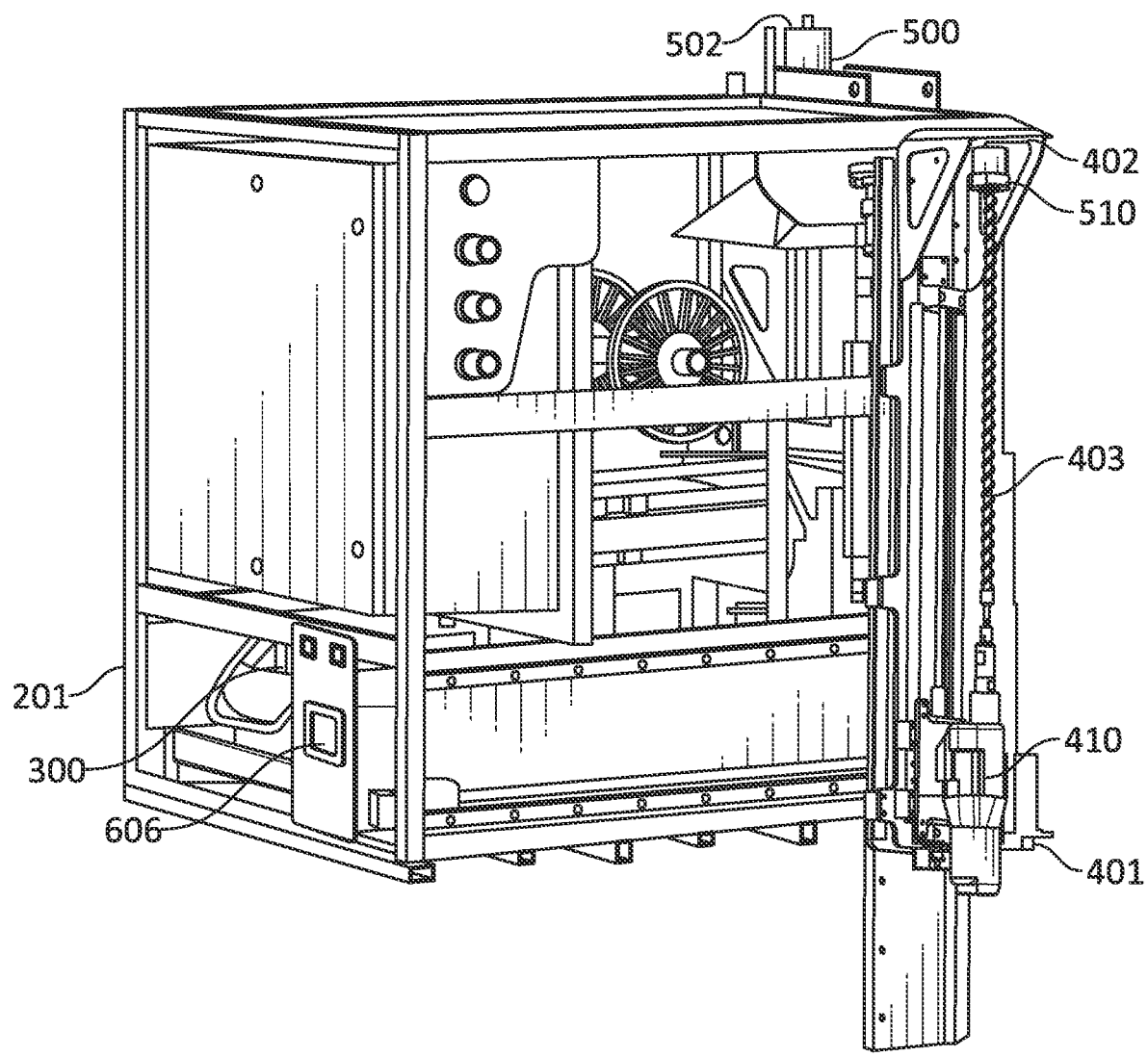
FIG. 6 shows an isometric rear side view of the sampling system with extraction arm inverted, according to the present disclosure.
Figure 7:
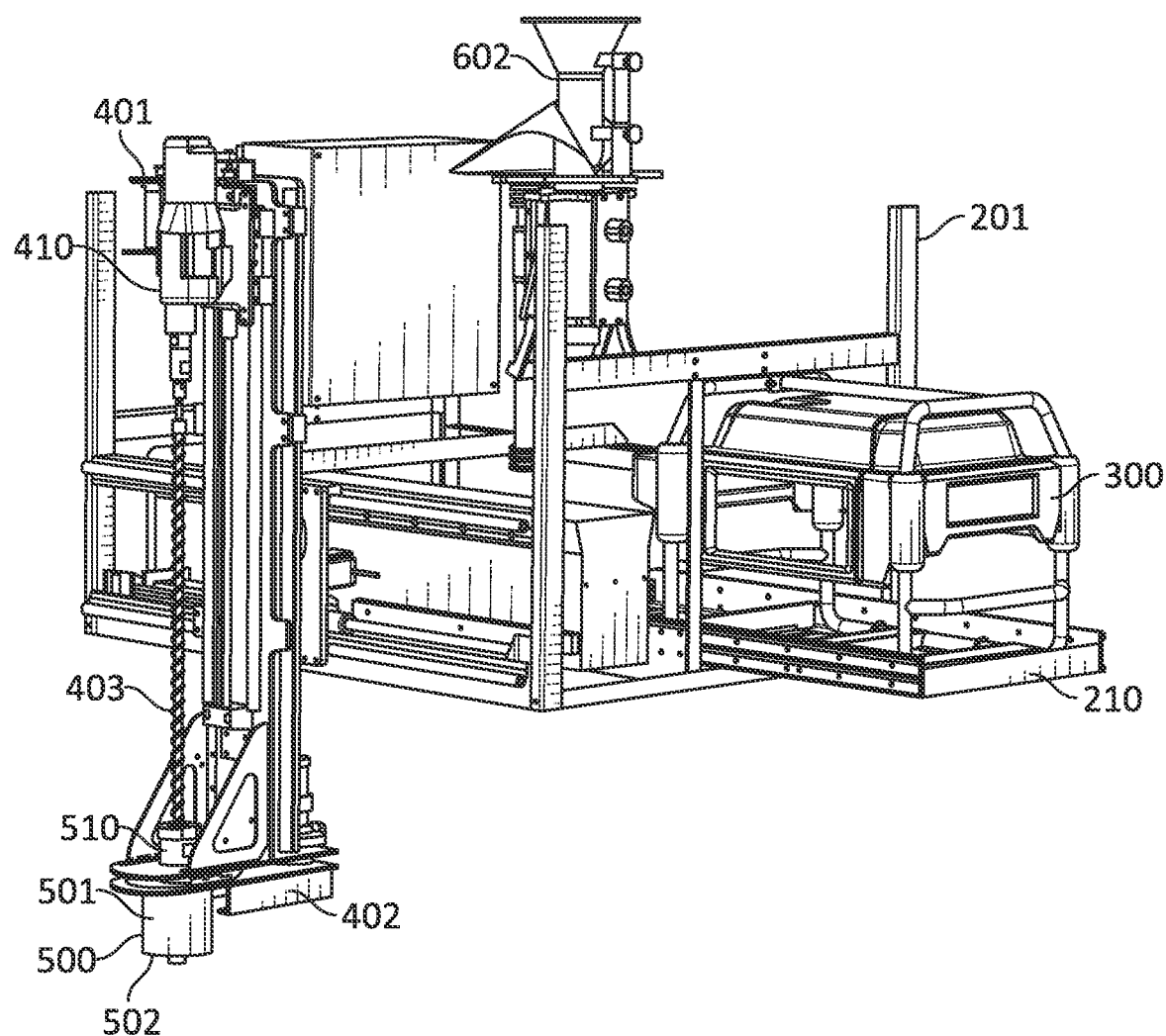
FIG. 7 shows an isometric side view of the sampling system with generator, according to the present disclosure.
Figure 8:
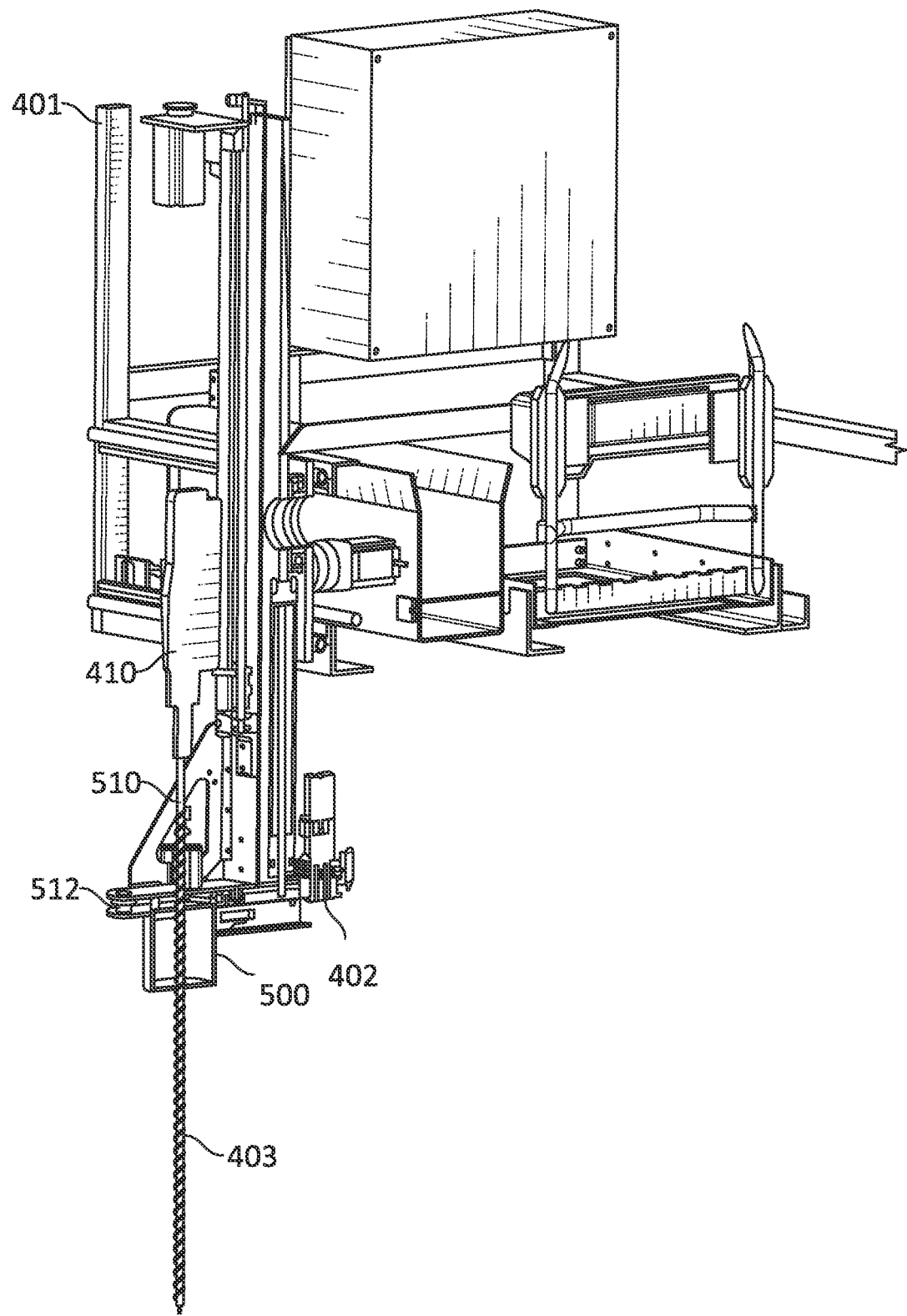
FIG. 8 shows a cross sectional view of the sampling system, according to the present disclosure.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the disclosure made herein.

Unless otherwise indicated, the words and phrases presented in this document have their ordinary meanings to one of skill in the art. Such ordinary meanings can be obtained by reference to their use in the art and by reference to general and scientific dictionaries.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the terms "include," "for example," "such as," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful, and is not intended to exclude other embodiments from the scope of the invention.

As used herein, the term "coupled" means the joining of two members directly or indirectly to one another. Such joining may be stationary in nature or movable in nature and/or such joining may allow for the flow of fluids, electricity, electrical signals, or other types of signals or communication between two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

Referring now to FIGS. 1-10, the autonomous soil sampler of the present disclosure is generally referred to as device 10. The device 10 is generally comprised of a vehicle 100 and a soil sampling assembly 200 received on the vehicle 100.

The vehicle 100 is generally adapted as an autonomous, un-manned machine that is capable of driving to a designated location for various soil extraction, sampling, packaging, and other diagnostics of nutrients and physical characteristics of a given quantum of soil. Although in the preferred configuration the vehicle 100 is autonomous, the vehicle could be driven by an operator for sampling. The vehicle 100 includes a platform 101 generally providing a base for the placement of the sampling assembly 200 of the device 10. In one embodiment, the platform 101 can be a part of any all-terrain vehicle 100 commonly utilized as a multipurpose, rugged utility vehicle, such as a Kubota RTV, a John Deere Gator, a Polaris Ranger, Kawasaki Mule, Bobcat 3400 or a similar vehicle, such as small tractor, that comprises a bed forming the platform 101 that may be used to support the soil sampling assembly 200 and having traction members 110 contacting the ground surface for generally moving the vehicle 100. To that end, the vehicle 100 includes a controller 102 coupled with and adapted to control various systems to aid in the autonomous driving and operation of the vehicle 100, including, but not limited to, obstacle detection and obstacle avoidance software and hardware features 103, navigational and positioning software and hardware features 104, including a GPS (Global Positioning System), wherein the vehicle 100 systems have the capability to detect pot holes, ditches, humans, animals, rough patches, mud holes, severe grade, etc. Accordingly, if the vehicle 100 controller 102 and systems cannot plan a path or navigate around a certain obstacle, it will simply wait for the obstacle to move or for a human operator to resolve the issue. Alternately, the vehicle 100 and device 10 can be driven and manipulated by the operator to specific sampling locations, wherein the operator may override certain controller 102 features and systems to enable this manual operation.

The device 10 vehicle 100 will likely have a specified operating boundary that it cannot leave. Before the device 10 enters a given field, the operator can retrieve an image of the field and overlay either a zone management map, soil map, yield map, or similar data input allowing the operator to generally provide the locations an in input 105 to the controller 102 to direct the device 10 to navigate autonomously to prepare the various sampling tasks. The operator may further input 105 the outside boundary of the field to designate the perimeter beyond which the autonomous soil sampler device 10 cannot travel. The operator will also input 105 any known obstacles that could cause harm, damage, or restriction to the autonomous device 10 or others for use by the controller 102 and obstacle avoidance system 103. Any other obstacles will likely be detected by the device 10 while traveling on the route. Maps or routes can also be loaded into the autonomous vehicle systems and controller 102 of the device 10 remotely through cellular or wireless data communications.

The obstacle avoidance system 103 may utilize light detection and ranging (LIDAR) systems from either a two dimensional (2D) or three dimensional (3D) pulse scan. Accordingly, the information detected through a LIDAR system may then be utilized by the obstacle avoidance system 103 to communicate through the controller 102 to other systems of the device 10 that an object may need to be avoided. Optionally, when driven by an operator, the vehicle 100 obstacle avoidance system 103 may be disabled.

The controller 102 is coupled to the additional systems of the device to generally control and operate the function of these systems, including, but not limited to, the vehicle 100, the soil system 200, a generator 300, an extraction arm 400, a bucket 500, a packaging assembly 600, and a transfer system 700.

The platform 101 of the vehicle 100 allows the soil sampling system 200 to be utilized in an efficient manner and for alternate uses. Accordingly, the soil sampling system 200 generally functions as a stand-alone unit that can be adapted for easy removal and installation onto the vehicle 100. Due to the size and weight of the soil sampling system 200 it is likely that the system 200 will need to be lifted with customary equipment for handling heavy equipment, such as a forklift, or by using manpower from multiple individuals. The platform 101 can then be used for other regular farm tasks when the system 200 is not present on the platform 101. Alternately, the platform 101 may be modified for the specific purpose of soil sampling with an integrated soil sampling system 200 or wherein the system 200 is provided in a purpose-built machine adapted to follow crop rows to perform in-season soil or nitrate sampling.

The soil sampling system 200 is generally provided in a housing 201 forming a frame and generally including a structure allowing for the securing and of the various mechanisms of the system 200. The housing 201 including a rack 210 sized and configured for the placement of a generator 300. The generator 300 generally a stand-alone generator as is known in the art and capable of providing an electrical current to the sampling system 200 to power the various mechanisms of the system 200.

The soil sampling system 200 generally utilizes an auger 403 to recover a desired amount of soil at a predetermined desired depth for sampling. The auger 403 is provided in assembly adapted to selectively rotate the auger 403 in a clockwise and counter-clockwise direction relative to a surface a given sample is desired to be extracted from. The auger 403 is positioned on a probe 410. The probe 410 movable along a height of the soil extraction arm 400 along a first rail of a pair of rails 404 extending along the height of the extraction arm 400, wherein the probe 410 is generally adapted to move the auger 403 to a given depth of penetration for generally extracting a quantum of soil for sampling. The extraction arm 400 having a first end 401 and a second end 402 opposed the first end 401, the distance between the first end 401 and the second end 402 defining the height of the extraction arm 400. Accordingly, the probe 410 is adapted to manipulate the auger 403 within the extraction arm 400 along the height to a depth of at least 12 inches into the soil (a depth known to facilitate nitrate sampling). In another exemplary embodiment, the probe 410 is adapted to manipulate the auger 403 to a depth of at least 24 inches into the soil.

The soil extraction arm 400 is positioned on the housing 201 and including the pair of linear rails 404 perpendicular to the housing 201 wherein the extraction arm 400 may be in a fixed position along the housing 201 or alternately capable of traversing a horizontal distance of the housing 201 generally parallel to the surface being sampled through movement of the pair of linear rails 404. Accordingly, the extraction arm 400 is capable movable to a transport position, a sampling position, and a packaging position, wherein the arm 400 may be moved both horizontally about the housing 201 parallel to the surface being sampled and downward and upward about the pair of linear rails 404 generally perpendicular to the surface to accommodate certain tasks at these positions. The soil extraction arm 400 includes the pair of linear rails 404 positioned on the housing 201 and generally aligned at a side of the vehicle 100 platform 101 to be movable into a close proximity with the soil surface to be sampled with the second end 402 positioned adjacent to the surface for sampling. In one embodiment, the soil extraction arm 400 sampling position enables soil sampling through movement of the probe 410 about one rail of the pair of linear rails 404 perpendicular to the surface to be sampled and movement of the bucket 500 about a second rail of the pair of rails 404 perpendicular to the surface to be sampled and positioned adjacent the probe 410 to receive an aliquot of sampled soil.

Accordingly, the sampling bucket 500 is movably received about the second rail of the pair of rails 404 of the extraction arm 400 and movable along the extraction arm height and generally adapted to collect the extracted soil for sampling. The sampling bucket 500 having a first end 501 and a second end 502, the first end 501 and second end 502 in communication with a sidewall to generally define the shape of the bucket and forming a cavity with an interior and having a volume within the interior of the sampling bucket 500 for the placement of extracted soil. The first end 501 and the second end 502 of the sampling bucket 500 each having a central aperture in alignment with each other and the auger 403 positioned on the probe 410, wherein the auger 403 passes through the interior of the sampling bucket 500 for contacting the ground surface and depositing extracted soil within the sampling bucket 500 interior.

In an alternate embodiment, the device 10 may be provided with a pair of sampling buckets 500. The pair of sampling buckets 500 generally functioning and placed similar to a configuration with a single sampling bucket. The pair of sampling buckets 500 provided to allow for the sampling of soil at a common extraction from multiple depths. Accordingly, a first sampling bucket 500 may receive a quantity of soil up to a first depth and a second sampling bucket may receive a second quantity of soil up to a second depth.

The first end 501 of the sampling bucket 500 is aligned with a cleaning collar 510. The cleaning collar 510 positioned adjacent to the first end 501 aligned with the central aperture on an exterior of the sampling bucket 500 and generally operating as a cleaning mechanism to generally scrape the auger 403 of collected material that may be brought up by the auger 403 after probing the soil. This cleaning collar 510 helps ensure a quality sample is obtained within the sampling bucket 500 and also cleans off the auger 403 prior to obtaining the next soil sample.

Figure 9:
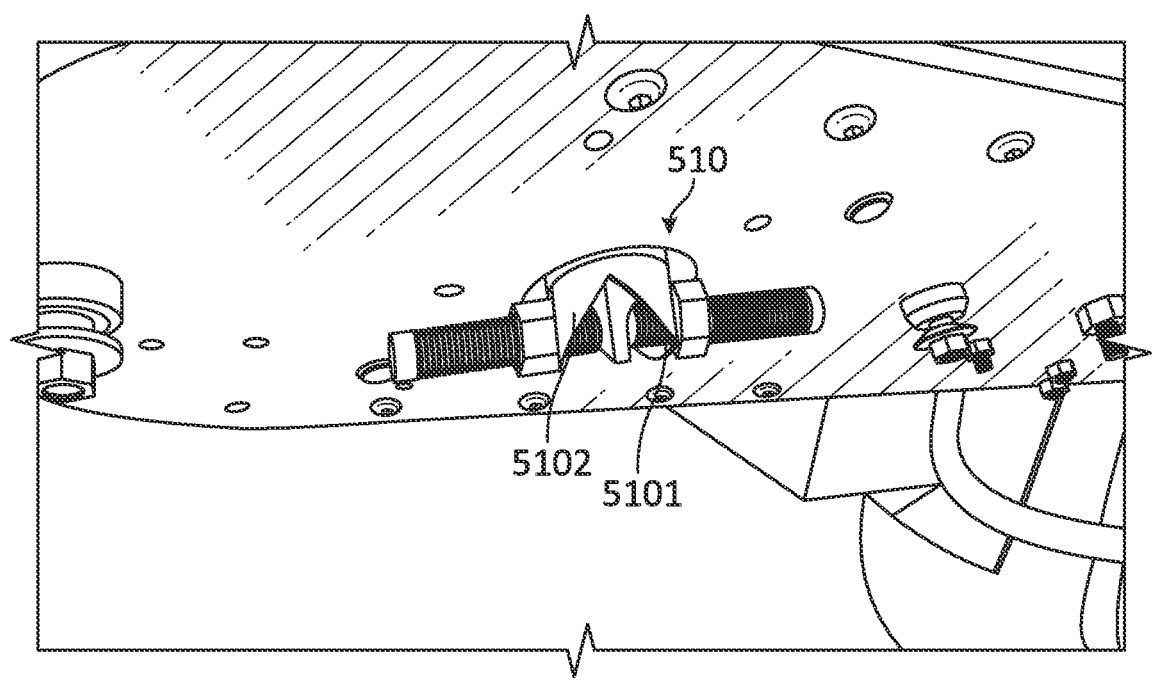
FIG. 9 shows an isometric bottom side view of the cleaning collar, according to the present disclosure.
Figure 10:
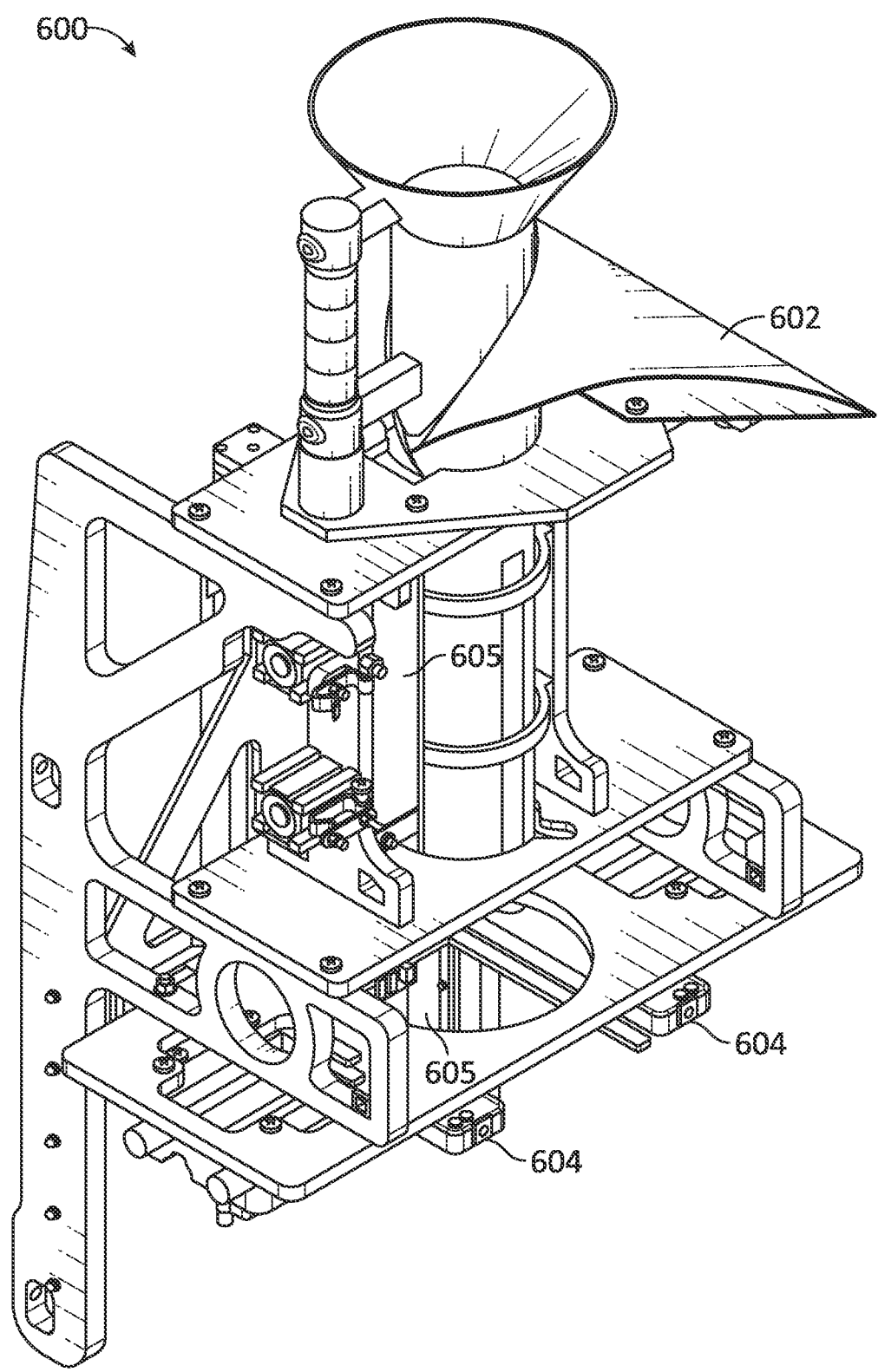
FIG. 10 shows an isometric view of a portion of the packaging assembly, according to the present disclosure.

In one embodiment, as shown in FIG. 9, the cleaning mechanism of the cleaning collar 510 is provided through the use of a bearing 5102 moving rotationally along with the auger 403 that includes a pair of removable nubs 5101 movably received perpendicular to the auger 403. The nubs 5101 are adapted for adjustment and generally sized for receipt within the helical groove, sometimes referred to as a flute, of the auger 403. Preferably, the nubs 5101 are constructed out of a plastic material and adapted for adjustment and replacement as they wear during use. Accordingly, the nubs 5101 can be adjusted in proximity to the helical groove of the auger 403 to remove more or less material from the auger 403 or adjusted to accommodate varying types of soils being extracted.

A sealing means 511 is positioned in a movable coupling with the first end 501 of the sampling bucket 500 and positioned between the collar 510 and first end 501 to close the first end 501 of the bucket 500 to enable transport of the sampled soil to the packaging assembly 600. Preferably, the sealing means 511 is a pair of plates 512 in a hinged coupling and movable from an open position adapted to allow for passage of the auger 403 to a closed position to generally seal the extracted soil within the sampling bucket 500. Accordingly, the sampling bucket 500 second end 502 is coupled to the transfer system 700 through at least one hose 701 in a coupling with the second end 502 between the bucket 500 and packaging assembly 600.

The transfer system 700 most generally configured as a means to transfer the sampled soil from the bucket 500 to the packaging assembly 600. Preferably, the transfer system 700 is a vacuum system to draw soil into the packaging assembly 600. Alternately, the transfer system 700 may utilize a combined blowing/vacuum system to create a zero pressure differential at the bucket 500 to prevent the introduction of unwanted debris into the packaging assembly 600. Still alternately, the transfer system 700 may be a mechanical means or operator transfer.

The packaging assembly 600 is generally positioned within the housing 201 and adapted to generally allow for the placement of a soil sample collected within the bucket 500 into a separate container, in the form of a package 607, for collection and analysis. Preferably the packaging assembly 600 utilizes a sealed form and fill concept thought the use of a reel 601, a forming collar 602, a forming tube 603, a gripper 604, and sealing member 605 in a coupling with the package 607. The package 607 preferably a plastic film, such as, but not limited to low density polyethylene film. Preferably, the package 607 is polyethylene tubing roll. The packaging assembly 600 further adapted to allow for packaging and labeling of samples. Although the reel and roll assembly for packaging is preferred, the package 607 can be any container utilized to store soil, such as, but not limited to, containers, bags, boxes, envelopes, or other similar items.

The reel 601 allows for the placement of the package 607 in a generally rolled configuration and aligned with an interior of the forming collar 602 and advanced through the forming tube 603 and positioned within the gripper 604 and sealing member 605, wherein the sealing member 605 and gripper 604 work in concert to generally seal and advance the package 607 through the collar 602 and tube 603 for the placement of individual samples. Accordingly, the samples are generally individually sealed in the package 607 in a sausage-like configuration for placement within a holding bin 606. Accordingly, this assembly maintains the individual soil samples in a connection within an individualized compartment of a larger sample sleeve. This sample collection configuration helps to main sample organization.

The package 607 is provided with a printing surface on an exterior portion for generally receiving an identifying mark from a printer. The sealed and printed sample compartments of the package 607 are then conveyed to the holding bin 606.

The packaging machine assembly 600 can additionally utilize an integrated barcode reader to read pre-printed compartments of package 607 or formed bags in place of a printer.

The forming collar 602 positioned within the housing 201, wherein the bucket transfer system 700 at least one hose 701 is an alignment with the forming collar 602 for placement of the sample. The package 607 generally assembled from a sheet, wherein the gripper 604 advances the package 607 over the collar 602 where the sheet is sealed both vertically and horizontally through the sealing member 605 to allow for placement of the sample.

The gripper 604 is adapted to move or advance the package 607 through the collar 602 and off of the reel 601. Accordingly, the gripper 604 is positioned below the reel 601 and having a pair of jaws to grip the package 607 and move the package 607 through the forming tube 603.

Preferably the gripper 604 is positioned below the forming collar 602 and movable in a direction perpendicular to the ground surface.

In an alternate embodiment, the packaging assembly 600 can be replaced by the operator, wherein the bucket 500 can be accessed manually by the operator after sampling and transferred to a separate bag or container as the package 607 and labelled. In this alternate configuration, the bucket 500 is movable along the second rail of the pair of linear rails 404 and positioned adjacent to a cab of the vehicle 100 the device 10 is placed upon, wherein the operator can access the bucket 500 from within the cab for manual collection.

In yet another alternate embodiment, the packaging assembly 600 can be replaced with a soil analyzer, wherein the bucket 500 and transfer system 700 can move the soil sample directly into the soil analyzer for direct analysis. The analyzer can analyze and determine the characteristics of the soil sample in real time. A computer system communicatively coupled to the analyzer can record and transmit the data recorded and relate the data to a specific location of the tested property. Additionally, the system can provide real-time updates as the soil samples are taken and packaged allowing a user to monitor the progress of the sampler. In one exemplary embodiment the sampler auger 403 can enter into the exact same hole to bag or analyze different and separate profiles of the soil (e.g. bag up 0-6" differently than 0-12" or 12-24"). This allows for a layered analysis of the soil at the sample point.

In another alternate embodiment, the packaging assembly 600 can still bag the samples from the bucket 500 and establish a queue to be analyzed by the analyzer as the sampler collects additional samples. Samples that are analyzed can then be discarded back into the field or re-bagged for further testing. This can allow for greater efficiency in the collection and analysis process.

The autonomous soil sampler 10 can be used for various other applications such as: a) autonomous cover crop seeding, b) nutrient analysis of the soil (e.g. pH, H, P, K, OM, Mg, CA, etc.), c) physical soil characteristics of soil (e.g. filtration, compaction layers, CEC, etc., d) autonomous in-season tissue sampling, e) "follow-m options" to follow any other piece of equipment such as tiling, spraying, rock pick-up, f) autonomous field rock removal, g) un-manned and autonomous chemical spraying, h) autonomous field topography, i) one-row corn planting for planting the male row in seed corn production, and j) population counter for plants that are just emerging out of the ground. In some embodiments, the soil sampler 10 can be tasked with doing multiple application in a single pass of the field to optimize efficiency. In other embodiments, the soil sampler 10 can take real-time measurements of other factors while obtaining the soil samples.

In another embodiment of the present disclosure, the use of LIBS (Laser-Induced Breakdown Spectroscopy) or other forms of LA-ICP-MS (Laser Ablation Inductively Coupled Plasma Mass Spectrometry) may be implemented on or off the platform 101 to expand the capabilities beyond the autonomous soil sampler 10. The soil can be extracted the same way with the auger 403 and arm 400 and then pelletized or mixed with a paraffin or other solution. The pellets can then be placed into an analytical system, such as a laser system, to be analyzed. An additional soil container also has the capabilities to perform pH testing.

For tissue sampling, the device 10 can navigate down crop rows and perform tissue sampling and nitrate testing at the same time. A tissue sampling arm can detect where the crop is located and retrieve a sample of leaf tissue. The tissue will then be dropped into the LIBS machine to acquire a quantification of the elements.

The LIBS machine can also be placed in the back of a truck or a similar vehicle to manually test the soil or tissue, while the device 10 travels and retrieves needed samples. These additions for tissue sampling can be made small enough to perform plant analysis all through the growing season. The machine can also use ISFET (ion-sensitive field-effect transistor) or ISE (ion-selective electrode) sensors to measure certain elements such as Nitrate, Ammonium, P, K, etc.

Additionally, electrical conductivity, Raman Scattering, Lab on Valve (LOV), FIA (Flow injection Analysis), X-ray, Vibrational Spectroscopy, or other forms or spectrometry in addition to LIBS, ISE or ISFET sensors can be provided on the autonomous soil sampler 10. The soil conditioning equipment can be mounted to the platform 101 and coupled with the various systems as well to prepare the sample for a certain nutrient measurement. These preparations can include drying, grinding, insertion Hydrogen peroxide, blending, homogenizing, inserting nutrient extractants, pelletizing, etc.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) but that the invention will include all embodiments falling with the scope of the appended claims.

The invention claimed is:

1. An autonomous soil sampling device, the device providing for the automated collection of a soil sample from a surface, the device comprising:
   a vehicle, the vehicle adapted as an autonomous machine capable of maneuvering to a designated location, the vehicle including:
      a platform;
      at least one traction member, the at least one traction member contacting the surface for moving the vehicle;
      a navigation and positioning system; and
   a soil sampling system, the soil sampling system positioned on the platform, the system including:
      a housing, the housing forming a frame;
      an extraction arm, the extraction arm received on the housing and having a pair of opposed ends, the distance between the ends defining a height, the extraction arm including:
         a probe, the probe movable along the height of the extraction arm; and
         an auger, the auger in communication with the probe and adapted for rotation, wherein the auger is directed into the surface for extracting a quantity of soil;
      a bucket, the bucket movable along the height of the extraction arm, the bucket including:
         a cavity, the cavity configured to receive the quantity of soil; and
         a cleaning collar, the cleaning collar received on an end of the bucket, the cleaning collar in communication with the auger to clean the auger of the collected quantity of soil;

a packaging assembly, the packaging assembly adapted to receive the quantity of soil from the bucket into a container; and a transfer system coupled between the bucket and the packaging assembly, the transfer system configured to move the quantity of soil from the bucket to the packaging assembly, wherein the transfer system is a vacuum; and a controller, the controller in selective communication with the navigation and positioning system, the soil sampling system, the extraction arm, the bucket, the transfer system, and the packaging assembly, wherein the controller directs the movement and operation of the device.

2. An autonomous soil sampling device, the device providing for the automated collection of a soil sample from a surface, the device adapted for placement on a vehicle, the device comprising:

a housing, the housing forming a frame;

an extraction arm, the extraction arm movably received on the housing and having a pair of opposed ends, the distance between the ends defining a height, the extraction arm including:

a probe, the probe movable along the height of the extraction arm; and an auger, the auger in communication with the probe and adapted for rotation, wherein the auger is directed into the surface for extracting a quantity of soil;

a bucket, the bucket movable along the height of the extraction arm, the bucket including:

a cavity, the cavity configured to receive the quantity of soil; and a cleaning collar, the cleaning collar received on an end of the bucket, the cleaning collar in communication with the auger to clean the auger of the collected quantity of soil;

a transfer system, the transfer system configured to move the collected soil to a packaging assembly;

the packaging assembly, the packaging assembly adapted to receive the quantity of soil from the transfer system, the packaging assembly including:

a package, the package positioned to receive the soil from the bucket; and a holding bin; the holding bin having an interior to receive the package; and a controller, the controller in communication with the extraction arm, the bucket, and the packaging assembly, wherein the controller directs the movement and operation of the device.

3. The device as in claim 2, wherein the transfer system is a vacuum.

* * * * *